(12) United States Patent
Kitazawa et al.

(10) Patent No.: US 11,672,481 B2
(45) Date of Patent: Jun. 13, 2023

(54) BIOLOGICAL INFORMATION MEASURING GARMENT

(71) Applicant: TOYOBO CO., LTD., Osaka (JP)

(72) Inventors: Yuko Kitazawa, Shiga (JP); Yuichiro Omote, Osaka (JP)

(73) Assignee: TOYOBO CO., LTD., Osaka (JP)

( * ) Notice: Subject to any disclaimer, the term of this patent is extended or adjusted under 35 U.S.C. 154(b) by 208 days.

(21) Appl. No.: 16/626,417

(22) PCT Filed: Jul. 3, 2018

(86) PCT No.: PCT/JP2018/025168
§ 371 (c)(1),
(2) Date: Dec. 24, 2019

(87) PCT Pub. No.: WO2019/009276
PCT Pub. Date: Jan. 10, 2019

(65) Prior Publication Data
US 2020/0138374 A1 May 7, 2020

(30) Foreign Application Priority Data

Jul. 3, 2017 (JP) .............................. JP2017-130222
Jul. 3, 2017 (JP) .............................. JP2017-130223

(51) Int. Cl.
*A61B 5/00* (2006.01)
*A61B 5/25* (2021.01)
(Continued)

(52) U.S. Cl.
CPC .............. *A61B 5/6804* (2013.01); *A61B 5/02* (2013.01); *A61B 5/0531* (2013.01); *A61B 5/25* (2021.01)

(58) Field of Classification Search
CPC ....... A61B 5/6804; A61B 5/6805; A61B 5/25; A61B 5/02; A61B 5/0531; A61B 5/6823
See application file for complete search history.

(56) References Cited

U.S. PATENT DOCUMENTS 4,580,572 A * 4/1986 Granek ................ A61N 1/0456
600/388
2005/0261564 A1* 11/2005 Ryu ..................... A61B 5/6804
600/388
(Continued)

FOREIGN PATENT DOCUMENTS

CN 106510023 3/2017
JP 2014-226172 12/2014
(Continued)

OTHER PUBLICATIONS

Extended European Search Report dated Mar. 23, 2021 in corresponding European Patent Application No. 18827921.0.
(Continued)

*Primary Examiner* — Adam Z Minchella
(74) *Attorney, Agent, or Firm* — Wenderoth, Lind & Ponack, L.L.P.

(57) ABSTRACT

The purpose of the present invention is to provide a biological information measuring garment having excellent exterior design, and yet with high measurement accuracy. A biological information measuring garment is provided with an electrode support portion which is joined to a garment body with an amount of freedom and which preferably has a covered-binding structure (looped structure), wherein the amount of freedom of the electrode support portion is set in a predetermined range such that, even when an electrode is in contact with the skin and in a semi-fixed state, the outer side of the garment can accommodate natural movements. In addition, a garment includes at least: a cup portion which covers the female breasts; and a front body, the garment further including on the inside thereof an electrode support portion provided with an electrode for biological information measurement. The cup portion, the front body, and the electrode support portion are sewn together at the same position, and a measuring device is disposed so as to be (Continued)

hidden between the garment and the electrode support portion, thus providing a structure preventing the measuring device from being seen from the outside.

20 Claims, 23 Drawing Sheets

(51) Int. Cl.
*A61B 5/02* (2006.01)
*A61B 5/0531* (2021.01)

(56) References Cited

U.S. PATENT DOCUMENTS

| | | | |
|---|---|---|---|
| 2007/0073131 A1* | 3/2007 | Ryu | A61B 5/6805 600/389 |
| 2011/0184270 A1* | 7/2011 | Russell | A61B 5/6804 600/388 |
| 2012/0246795 A1* | 10/2012 | Scheffler | A61B 5/0002 2/243.1 |
| 2013/0053674 A1 | 2/2013 | Volker | |
| 2015/0067943 A1 | 3/2015 | Scheffler et al. | |
| 2015/0173639 A1* | 6/2015 | Ichida | A61N 1/0472 600/397 |
| 2015/0374251 A1 | 12/2015 | Yoshioka et al. | |
| 2017/0196514 A1* | 7/2017 | Moltani | A61B 5/6804 |
| 2018/0249767 A1* | 9/2018 | Begriche | A41D 13/1281 |
| 2019/0116892 A1 | 4/2019 | Scheffler et al. | |

FOREIGN PATENT DOCUMENTS

| | | | |
|---|---|---|---|
| JP | 2016/26547 | 2/2016 | |
| JP | 3202655 | 2/2016 | |
| JP | 2016-158912 | 9/2016 | |
| JP | 6114501 | 4/2017 | |
| WO | 02/074109 | 9/2002 | |
| WO | WO-02074109 A2 * | 9/2002 | ........... A61N 1/0484 |

OTHER PUBLICATIONS

International Search Report dated Sep. 11, 2018 in International (PCT) Application No. PCT/JP2018/025168.
Office Action dated Dec. 30, 2021 in corresponding Chinese Patent Application No. 201880044722.3, with English translation.
Office Action dated Apr. 5, 2022 in corresponding Japanese Patent Application No. 2019-527715, with English language translation.
Office Action dated Oct. 12, 2021 in corresponding Taiwanese Application No. 107122865, with English-language translation.
Office Action dated Apr. 6, 2022 in corresponding Taiwanese Application No. 107122865, with English-language translation.
Office Action dated Sep. 8, 2022 in corresponding Taiwanese Application No. 107122865, with English-language translation.
Decision of Rejection dated Sep. 6, 2022 in Japanese Patent Application No. 2019-527715, with English machine translation.
Office Action dated Sep. 26, 2022 in Chinese Patent Application No. 201880044722.3, with English machine translation.
Office Action dated Jun. 21, 2022 in corresponding Japanese Patent Application No. 2019-527715, with English translation.
Communication pursuant to Article 94(3) EPC dated Dec. 15, 2022 in corresponding European Patent Application No. 18827921.0.

* cited by examiner

[Fig. 1]
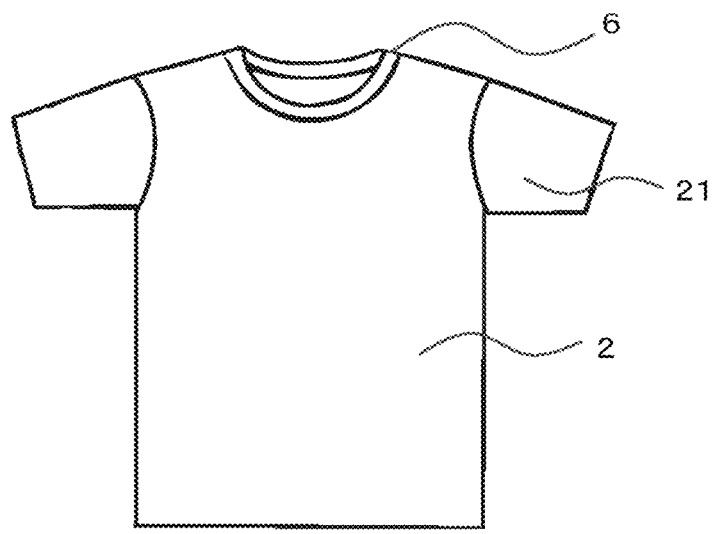

[Fig. 2]
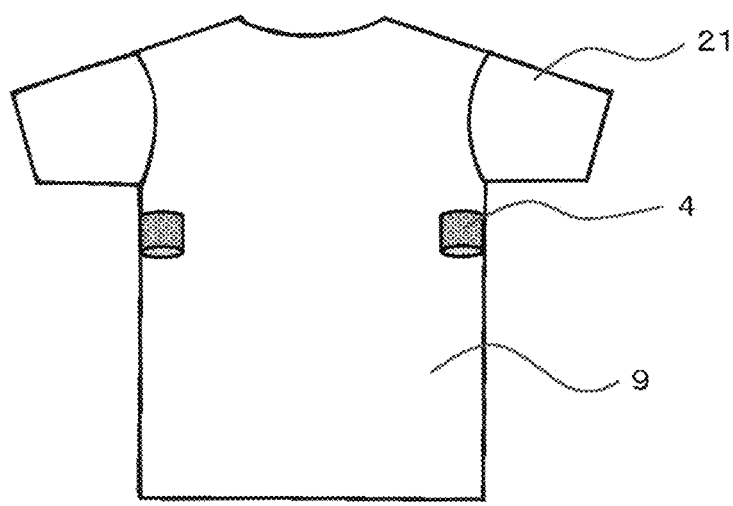

[Fig. 3]
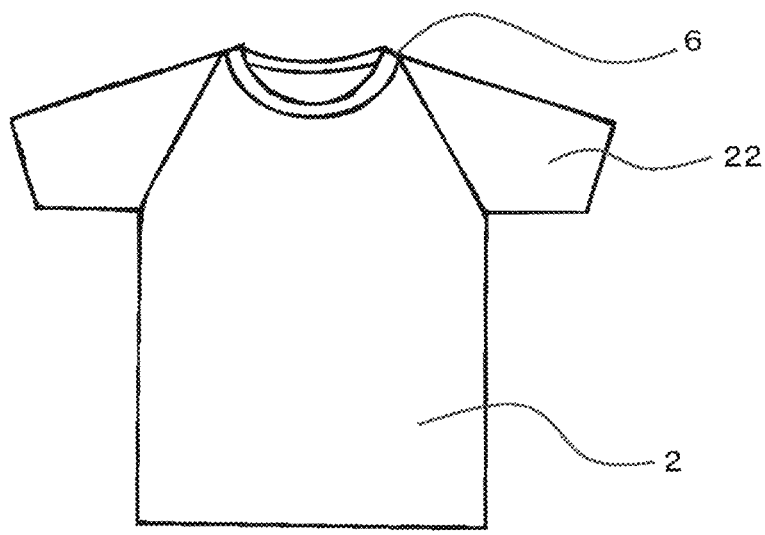

[Fig. 4]
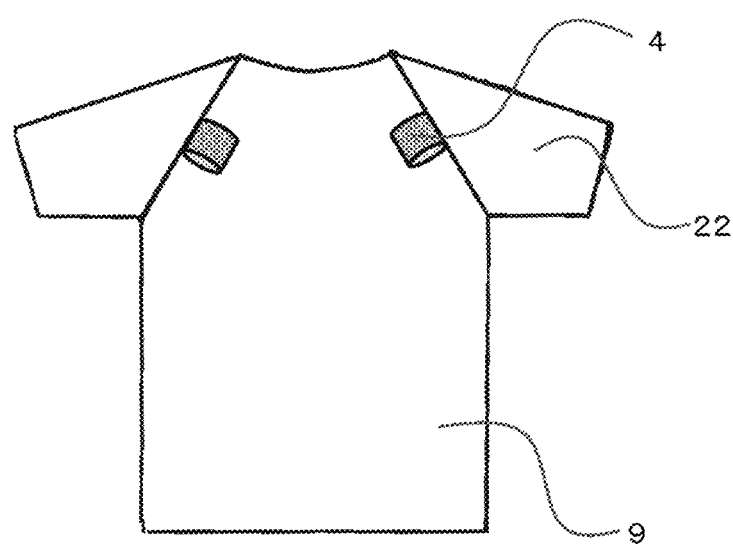

[Fig. 5]
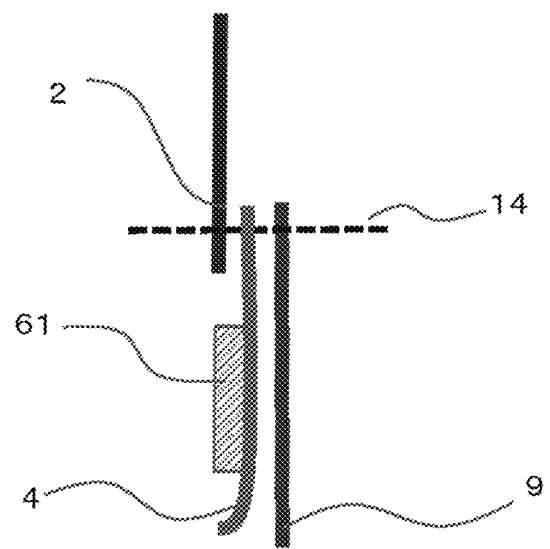

[Fig. 6]
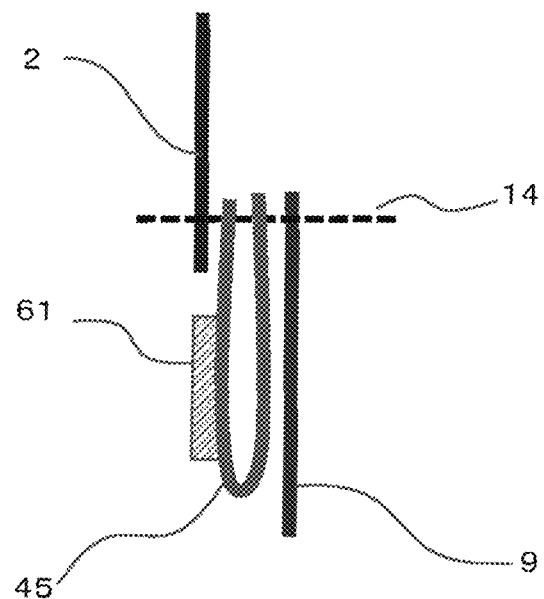

[Fig. 7]
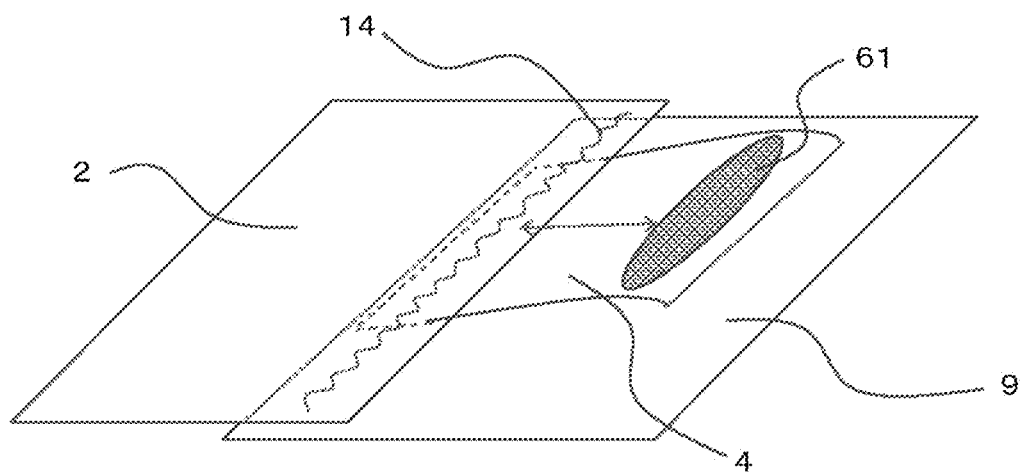

[Fig. 8]
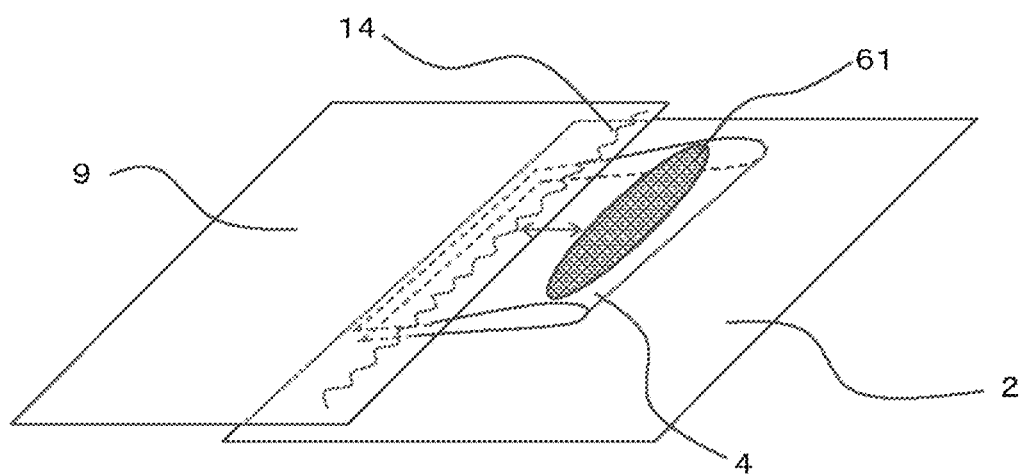

[Fig. 9]
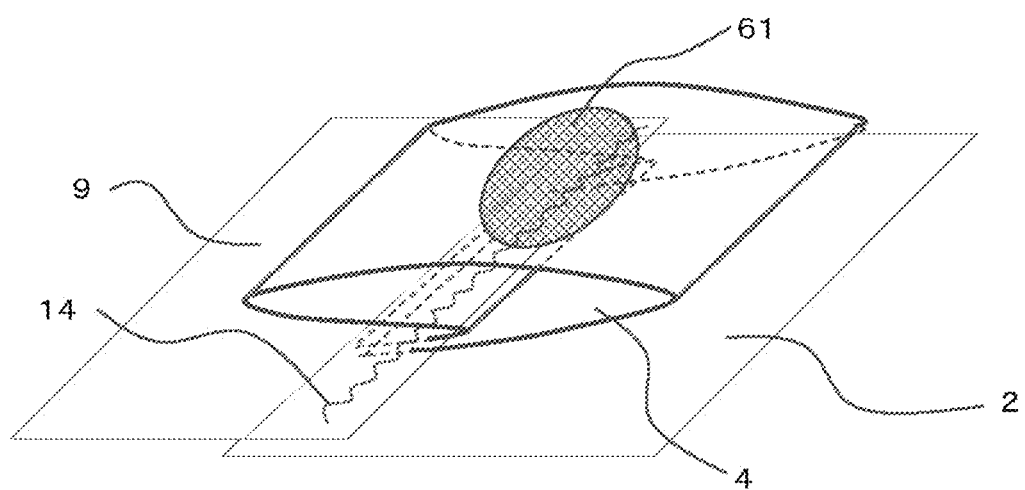

[Fig. 10]
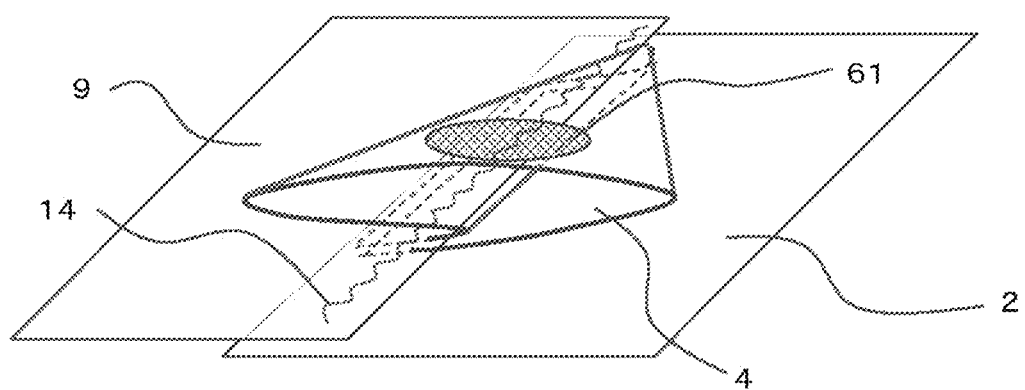

[Fig. 11]
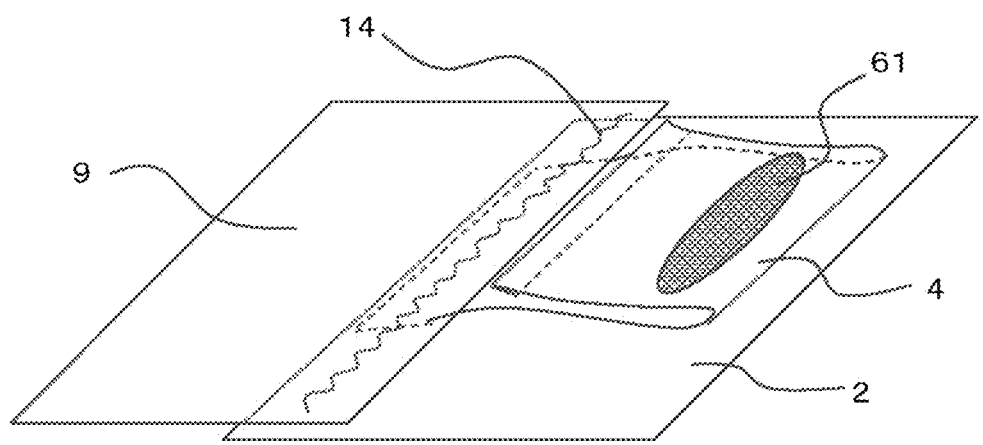

[Fig. 12]
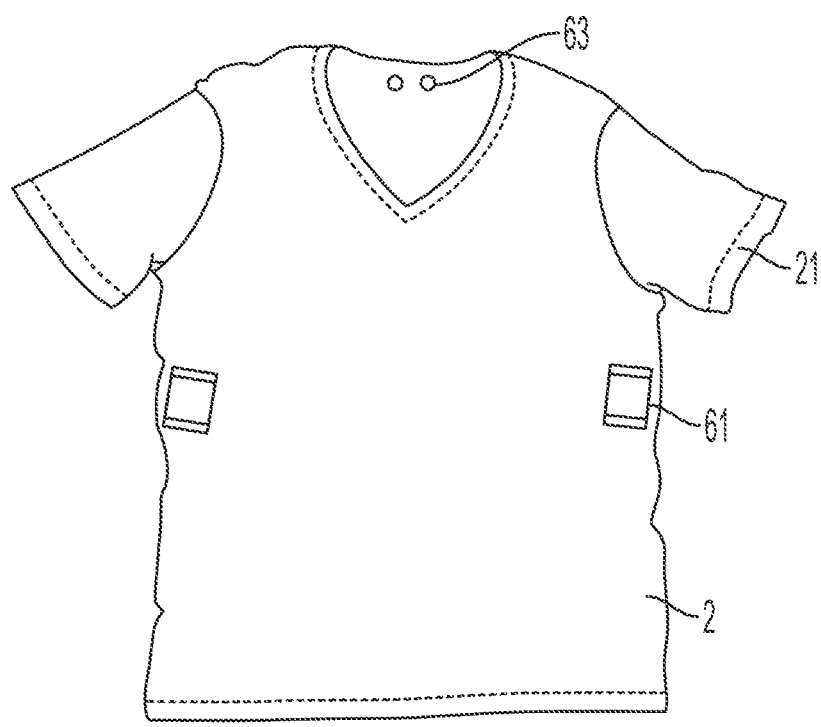

[Fig. 13]
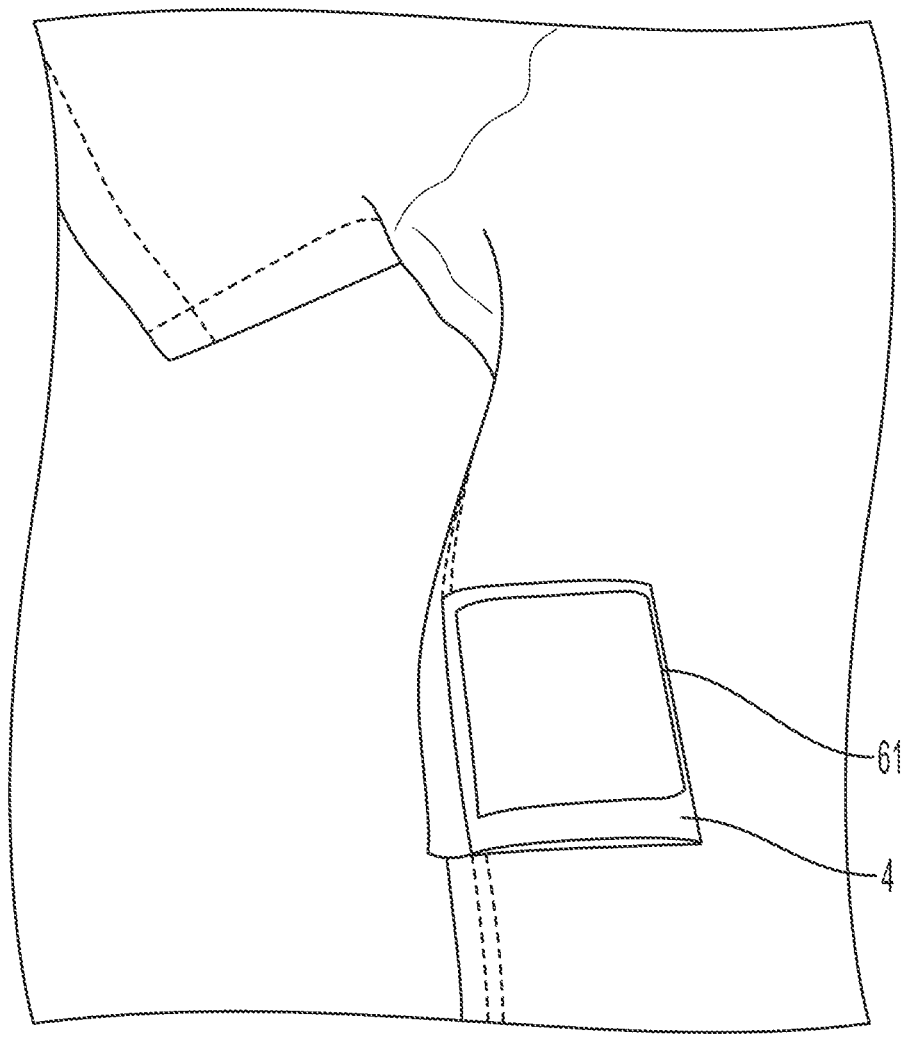

[Fig. 14]
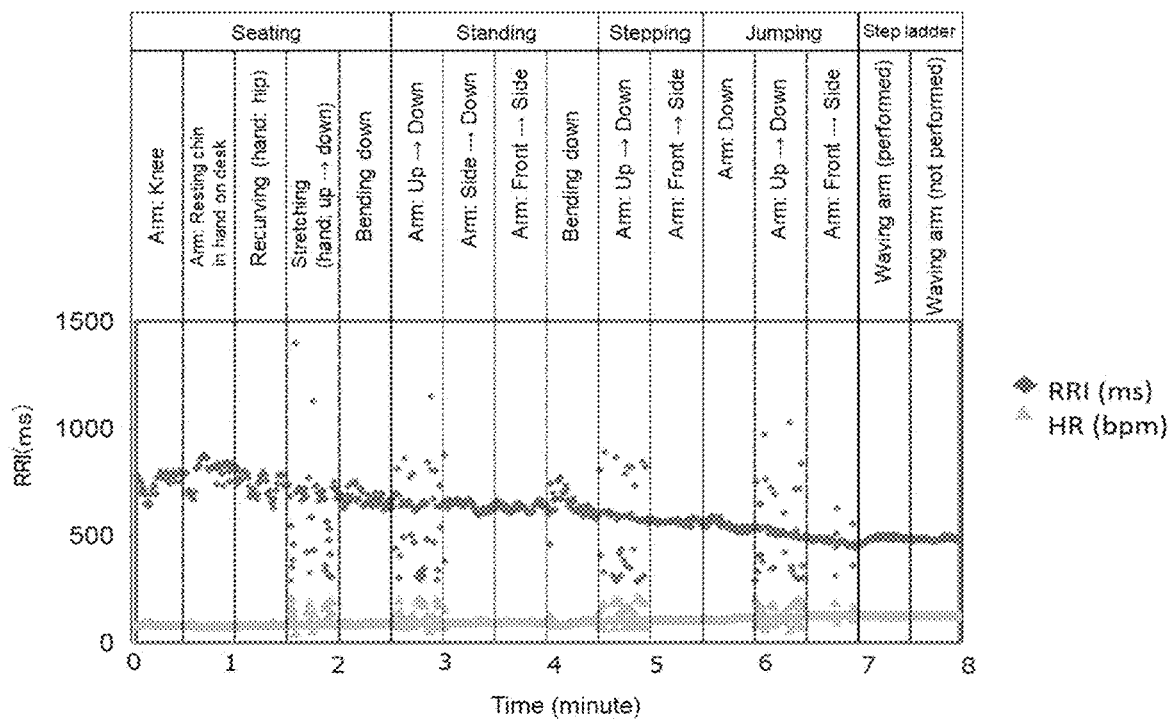

[Fig. 15]
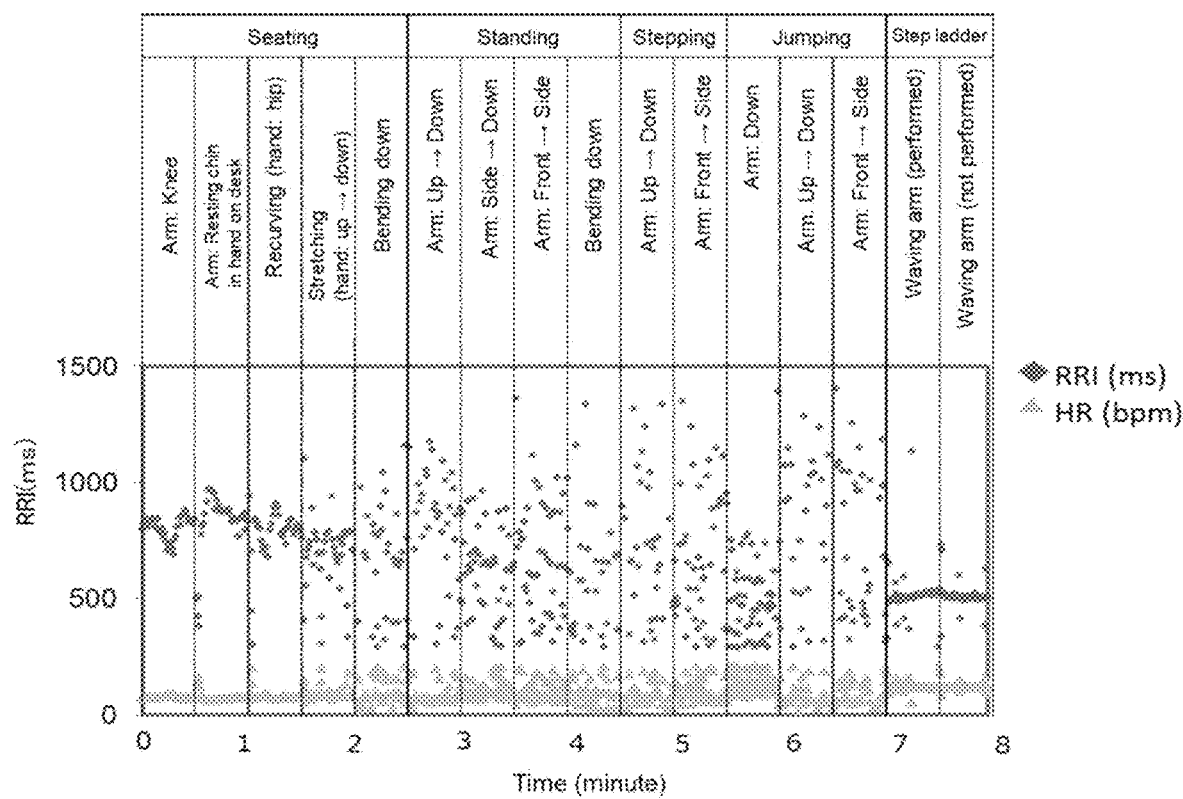

[Fig. 16]
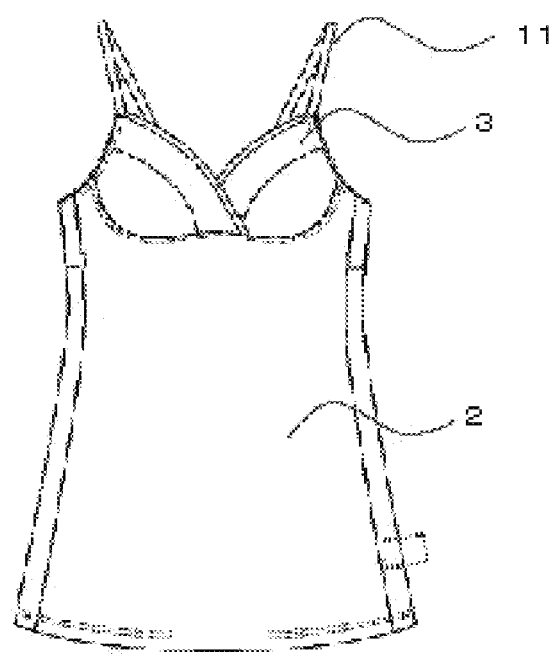

[Fig. 17]
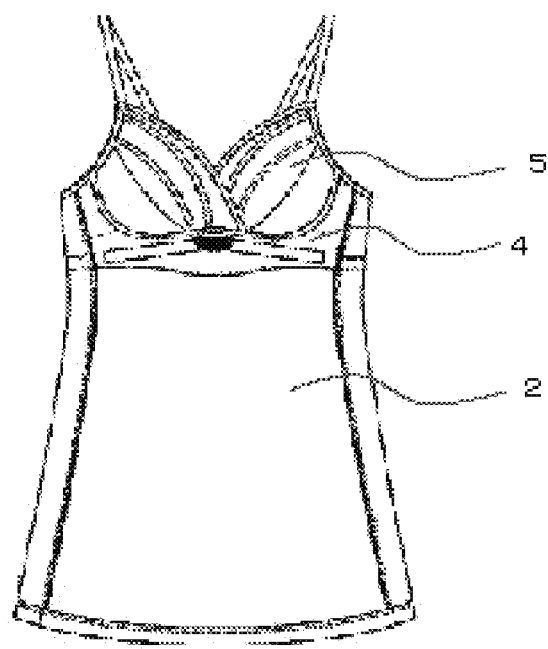

[Fig. 18]
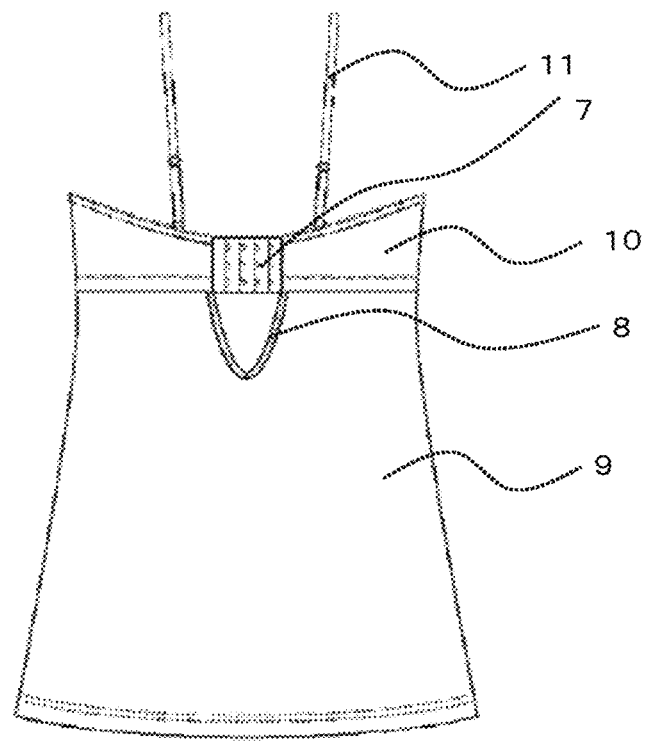

[Fig. 19]
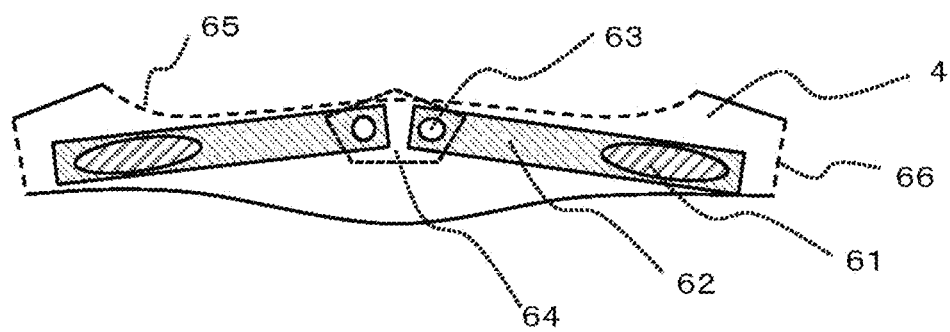

[Fig. 20]
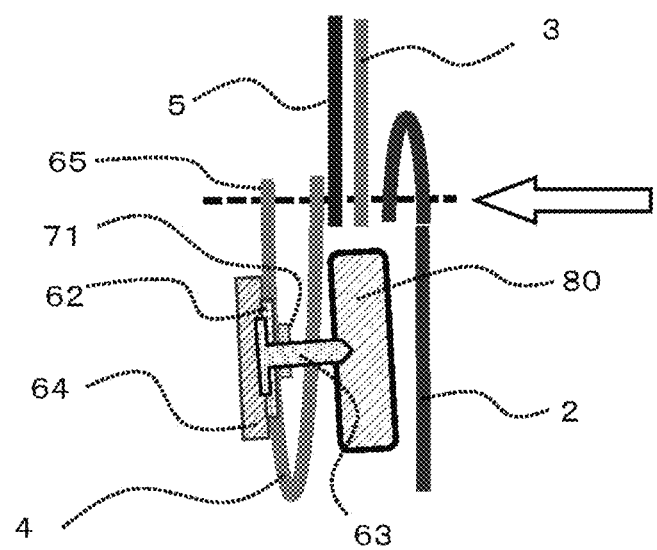

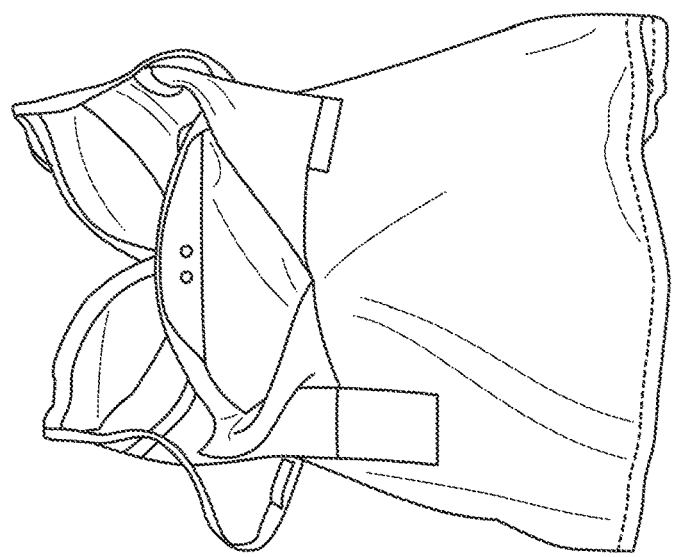
[Fig. 23]
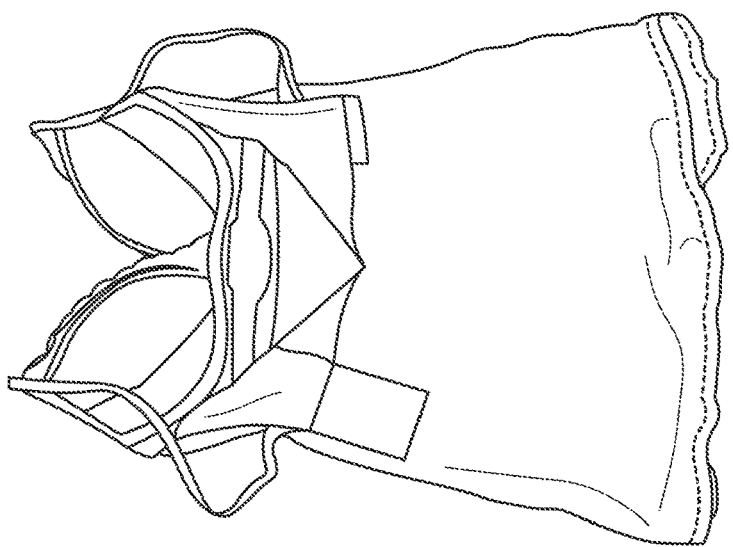
[Fig. 22]
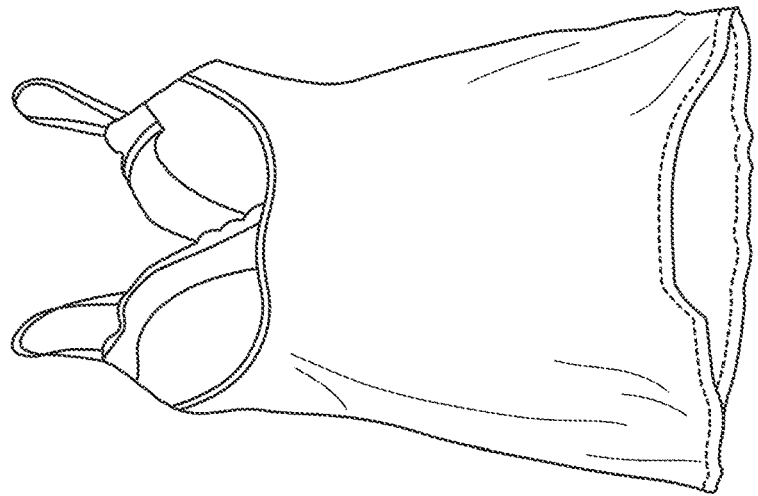
[Fig. 21]

[Fig. 24]
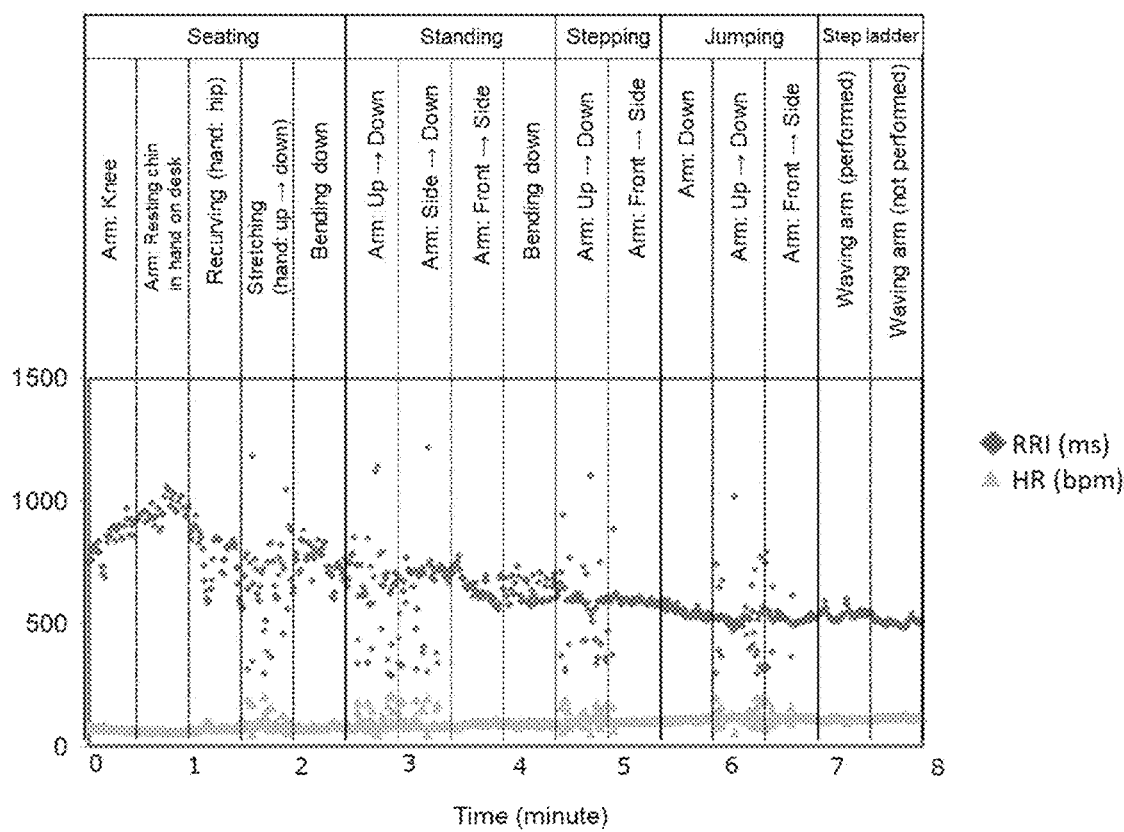

[Fig. 25]
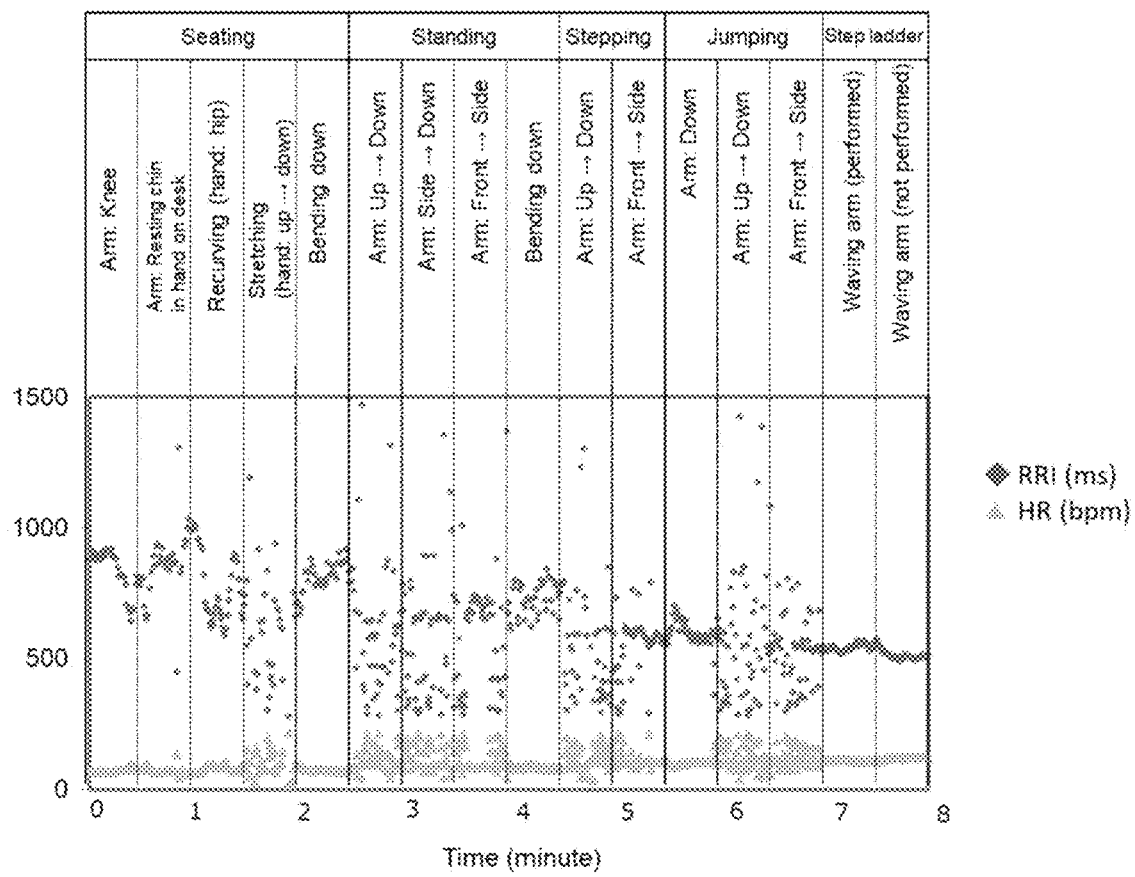

BIOLOGICAL INFORMATION MEASURING GARMENT

TECHNICAL FIELD

The present invention relates to a biological information measuring garment including at least an electrode in contact with a biological body.

BACKGROUND ART

Conventionally, as a method for measuring biological information, a method for measuring biological information of a human body such as an electrocardiogram is known. However, in the prior art, in order to fix the electrode, it is essential to use a gel or paste between the electrode and the skin surface, or to use an adhesive tape. For this reason, there is a problem that, in continuous measurement for a long time, unpleasant feeling due to sweating, itching and discomfort are generated, and a sticky electrode having high adhesiveness such as an adhesive tape is more likely to cause dermatitis.

On the other hand, in order to solve such a problem, an invention of a wearable biological information measuring device capable of easily measuring biological information such as an electrocardiogram by being worn as a garment has been made. However, although this invention has been improved in terms of unpleasant feeling due to sweating, generation of itching and discomfort, and dermatitis, it has not completely eliminated unpleasant feeling caused by touching the biological body with the electrode. Further, in the conventional wearable biological information measuring device, the measuring device is exposed (Patent Document 1), or the device part is not exposed, but the cover for covering the device is exposed (Patent Document 2). Therefore, there are restrictions on the design of the exterior.

PRIOR ART DOCUMENTS

Patent Documents

Patent Document 1: JP 6114501 B2

Patent Document 2: JP-A-2016-158912

SUMMARY OF THE INVENTION

Problems to be Solved by the Invention

As a result of diligent research to solve such problems, the present inventors have found that unpleasant feeling when wearing a garment having an electrode for biological information measurement is not because the electrode sticks to the skin, but the electrode sticks to the skin so that the positional relationship between the garment and the wearer's body is constrained. Then, the present inventors have found that, by increasing the positional freedom of the electrode portion located on the garment, even when the electrode position was fixed conversely, the positional freedom of the entire garment is relatively high and unpleasant feeling is greatly reduced, to thereby achieve the present invention.

Solutions to the Problems

That is, the present invention has the following configurations.

[1] A biological information measuring garment comprises a garment body and an electrode support portion including an electrode for biological information measurement,
wherein the electrode support portion includes a flexible fabric cloth as a base material,
wherein the electrode support portion is located on a side of the garment body that is in contact with a biological body,
wherein the base material of the electrode support portion has a joint side fixed to the garment body and a free side not fixed to the garment body, and
wherein, when a total of the joint side and the free side is a perimeter of the base material of the electrode support portion, a length of the joint side is 60% or less of the perimeter of the base material of the electrode support portion.

[2] The biological information measuring garment according to [1], wherein a shortest distance between the joint side of the base material and the electrode of the electrode support portion is in a range of 3 mm or more and 50 mm or less.

[3] The biological information measuring garment according to [1] or [2],
wherein the biological information measuring garment is a garment including at least a front body and a back body, and
wherein the joint side is sewn at the same position as a sewn portion of the front body and the back body.

[4] The biological information measuring garment according to [1] or [2],
wherein the biological information measuring garment is a garment including at least a sleeve portion and a body portion, and
wherein the joint side is sewn at the same position as a sewn portion of the sleeve portion and the body portion.

[5] The biological information measuring garment according to [1] or [2], wherein the joint side is sewn at the same position as a sewn portion of a neckline of the garment.

[6] The biological information measuring garment according to [1] or [2], wherein the joint side is sewn at the same position as a sewn portion of a cuff of the garment.

[7] The biological information measuring garment according to [1] or [2], wherein the joint side is sewn at the same position as a sewn portion of a portion around a waist of the garment.

[8] The biological information measuring garment according to [1] or [2], wherein the joint side is sewn at the same position as a sewn portion of a hem of the garment.

[9] The biological information measuring garment according to any one of [1] to [8], wherein the base material of the electrode support portion has an open bag structure (loop structure).

[10] The biological information measuring garment according to [9], wherein the open bag structure has two or more open portions.

[11] The biological information measuring garment according to [9], wherein the open bag structure has one open portion.

[12] The biological information measuring garment according to any one of [9] to [11],
wherein the base material of the electrode support portion has the open bag structure, and
wherein a position of the electrode is a location including a farthest position from a sewn portion on the base material.

[13] The biological information measuring garment according to [1], wherein the biological information measuring garment is a garment including at least a cup portion covering a chest part and a front body, wherein the biological information measuring garment further includes an electrode support portion including an electrode for biological information measurement inside the garment, and wherein the cup portion, the front body, and the electrode support portion are sewn at the same position.

[14] The biological information measuring garment according to [13], wherein the cup portion includes a front cup portion and a back cup portion, and wherein the front cup portion is made of the same fiber material as a fiber material of the front body.

[15] The biological information measuring garment according to [13] or [14], wherein the electrode support portion has a bag structure, and wherein a closing mouth of the bag is sewn at the same position as the cup portion, the front body, and the electrode support portion.

[16] The biological information measuring garment according to any one of [13] to [15], wherein a connector for connecting the electrode and a detachable electronic unit is located between the electrode support portion and the front body.

[17] The biological information measuring garment according to any one of [13] to [16], wherein the fiber material constituting the front body and the front cup portion is a knit material containing 50% or more of cotton.

[18] The biological information measuring garment according to any one of [13] to [17], wherein the biological information measuring garment has a rear opening structure, and includes a plurality of engagement portions for adjusting a size of the chest part at a rear opening portion.

[19] The biological information measuring garment according to any one of [13] to [18], wherein the electrode includes a wiring, and the electrode and the wiring are made of the same material.

[20] The biological information measuring garment according to any one of [13] to [19], wherein the electrode for biological information measurement is a conductive fabric.

Furthermore, the present invention is preferable to have the following configurations.

[21] The biological information measuring garment according to any one of [1] to [12], in which the electrode for biological information measurement is a conductive fiber composite material.

[22] The biological information measuring garment according to any one of [1] to [12], in which the electrode for biological information measurement is a stretchable conductive material.

[23] The biological information measuring garment according to any one of [1] to [12], [21], or [22], in which the electrode includes a wiring, and the electrode and the wiring are made of the same material.

Effects of the Invention

The present invention has a feature in that the electrode is not directly attached to the garment but is attached with a degree of freedom via an electrode support portion. The base material of the electrode support portion is a flexible fabric cloth, and is preferably made of a fabric cloth which is the same material as the garment, and the electrode for biological information measurement is attached to the base material by way of bonding, sewing, printing, transferring, or the like. Normally, the electrode support portion and the garment are joined together by sewing the entire periphery of the electrode support portion to the garment or bonding the entire surface with a hot melt adhesive. The present invention has a feature in that only a part of the electrode support portion is joined to the garment, and most of the electrode support portion including at least the portion where the electrode is attached is a free end. That is, by such a structure, the electrode portion has a degree of freedom with respect to the garment body. It is preferable that the electrode portion be in contact with the wearer's skin and desirably maintains stable electrical contact with the biological body without being deviated during measurement. In the present invention, the garment side has a degree of freedom relatively with respect to the electrode. Therefore, even when there is such a motion that the garment deviates from the body, and the garment actually deviates, this deviation is absorbed by the play of the electrode support portion, so that the electrode can maintain stable electrical contact with the biological body. Here, the play is a part between the joint portion (sewn portion) of the electrode support portion with the garment and the electrode end.

In the present invention, the joint portion between the electrode support portion and the garment body is overlaid on the sewn portion necessary for manufacturing the garment, and is sewn at the same position, thereby being capable of obtaining a biological information measuring garment excellent in design without forming a new seam or increasing the number of joint portions for providing a biological information measurement function.

According to the present invention, there is provided a biological information measuring garment which prevents the measuring device from being seen from the outside, and has excellent exterior design.

In addition, the biological information measuring garment of the present application can use a clothing fabric incorporating functionality and design as in a general garment. Conventionally, as the clothing fabric used for the biological information measuring garment, there have been used clothing fabrics suitable for arranging electrodes and having no unevenness capable of sufficiently fixing the electrodes, and thick and firm clothing fabrics. However, in the biological information measuring garment according to the present application, the electrode portion is installed on the electrode support portion. Therefore, the clothing fabric of the garment body is not subjected to a limitation by the electrode. Therefore, it is possible to select clothing fabrics according to the season and taste. There can be provided, for example, a biological information measuring garment using a grid-like clothing fabric with unevenness called waffle knit, which is superior in design and different from ordinary flat knit, and a biological information measuring garment using a fluttering and thin clothing fabric called georgette clothing fabric.

In addition, in the biological information measuring garment of the present application, when a cup portion and a front body are sewn together, the electrode support portion is sewn together at the same position. Therefore, a new seam by installing the electrode is not formed, aesthetics and design in exterior are not impaired, and there is no unpleasant feeling that the seam touches the skin. As for the unpleasant feeling, the biological information measuring garment requires the electrode portion to be in close contact with the biological body, so there is a problem of tightness due to tightening. In the biological information measuring garment of the present application, the length adjustment is possible by a rear opening structure, so that the electrode can be in close contact with the skin by moderate tightening matched with a wearer's body shape. In addition, since only the underbust part necessary for the close contact of the electrode is tightened, the breast and the abdomen part are not tightened and there is little unpleasant feeling.

The present invention has been promoted mainly for the improvement of aesthetics and design, but more unexpectedly, compared with the conventional biological information measuring garment in which the electrode is directly attached to the garment body clothing fabric, it is possible to obtain the effect of reducing noise during biological information acquisition. This is because in the conventional biological information measuring garment, the friction between the electrode and the biological body is also caused by the friction between the garment body and the body, but in the configuration of the present invention, it is assumed that the restraint from the garment body to the electrode portion is loosened, so that the friction between the electrode and the biological body is reduced.

BRIEF DESCRIPTION OF THE DRAWINGS

FIG. 1 is a schematic view showing an outer shape of a standard T-shirt which is an example of a biological information measuring garment according to the present invention.

FIG. 2 is a schematic view showing a state in which the biological information measuring garment shown as an example in FIG. 1 is turned back, and is an example in which electrode support bodies having a double-open bag structure are each sewn to a sewn portion of a front body and a back body.

FIG. 3 is a schematic view showing an outer shape of a raglan sleeve T-shirt which is an example of the biological information measuring garment according to the present invention.

FIG. 4 is a schematic view showing a state in which the biological information measuring garment shown as an example in FIG. 3 is turned back, and is an example in which electrode support bodies having a double-open bag structure are each sewn to a sewn portion of a raglan sleeve portion and the back body.

FIG. 5 is a cross-sectional view showing the positional relationship when the electrode support portion is sewn at the same portion as the sewn portion of the front body and the back body in the present invention.

FIG. 6 is a cross-sectional view showing the positional relationship when the electrode support portion having a bag structure is sewn at the same portion as the sewn portion of the front body and the back body in the present invention.

FIG. 7 is a schematic view showing the positional relationship when the electrode support portion is sewn at the same portion as the sewn portion of the front body and the back body in the present invention.

FIG. 8 is a schematic view showing the positional relationship when the electrode support portion having a bag structure with two openings is sewn at the same portion as the sewn portion of the front body and the back body in the present invention.

FIG. 9 is a schematic view showing the positional relationship when the electrode support portion having a bag structure is sewn at the same portion as the sewn portion of the front body and the back body in the present invention, and is a schematic view showing a case where a position of the electrode is at a location including a farthest position from the sewn portion on the base material of the electrode support portion.

FIG. 10 is an example of the case where the electrode support portion having a bag structure of the present invention is used, and is an example in which the bag is closed in a conical shape with one opening.

FIG. 11 is an example in which the electrode support portion is folded into a pocket shape when a single-leaf electrode support portion is used in the present invention.

FIG. 12 is an exterior photograph of a prototype of a T-shirt type biological information measuring garment as an example of the biological information measuring garment in the present invention.

FIG. 13 is an enlarged photograph of the vicinity of the electrode support portion in the prototype shown in FIG. 12.

FIG. 14 is a diagram showing results of electrocardiogram measurement in an example of the present invention.

FIG. 15 is a diagram showing results of electrocardiogram measurement in a comparative example of the present invention.

FIG. 16 is a view of a front outer surface of a camisole with a brassiere that is an example of the biological information measuring garment in the present invention.

FIG. 17 is a view of a front skin surface of the camisole with a brassiere that is an example of the biological information measuring garment in the present invention.

FIG. 18 is a view of a rear outer surface of the camisole with a brassiere that is an example of the biological information measuring garment in the present invention.

FIG. 19 is a detailed view of the electrode support portion attached to the camisole with a brassiere that is an example of the biological information measuring garment in the present invention.

FIG. 20 is a schematic view showing the positional relationship between a cross-sectional structure of the electrode support portion attached to the camisole with a brassiere that is an example of the biological information measuring garment in the present invention and a portion at which the garment body is sewn.

FIG. 21 is an exterior photograph of the prototype of the camisole with a brassiere that is an example of the biological information measuring garment in the present invention, which is taken from the surface side.

FIG. 22 is a photograph of the prototype of the camisole with a brassiere that is an example of the biological information measuring garment in the present invention, which is taken from the rear side, in which an engagement portion is disengaged and a rear opening portion is widened so that the electrode support portion can be seen.

FIG. 23 is a photograph of the prototype of the camisole with a brassiere that is an example of the biological information measuring garment in the present invention, which is taken from the rear side, in which the engagement portion is disengaged, the rear opening portion is widened, and the electrode support portion is turned back so that the snap hook functioning as a connector can be seen.

FIG. 24 is a diagram showing results of electrocardiogram measurement in an example of the present invention.

FIG. 25 is a diagram showing results of electrocardiogram measurement in a comparative example of the present invention.

MODE FOR CARRYING OUT THE INVENTION

The biological information in the present invention is an electrocardiogram, myoelectricity, body temperature, garment inner temperature, respiratory rate, respiratory state, sweating amount, sweating state, joint angle, displacement amount of each part of the body, the acceleration of each part of the body, the position information of each part of the body, and the like, which can be detected by electrodes and other sensors. The electrodes and/or other sensors are appropriately selected according to biological information to be measured. Among these, it is preferable that the present invention include at least a plurality of electrodes that are in contact with a biological body, and it is further preferable that the present invention include an electrode capable of measuring an electrocardiogram as biological information. In general, the electrocardiogram measurement results are generally recorded as an electrocardiogram and an electrocardiogram waveform in which time is plotted on the horizontal axis and potential difference is plotted on the vertical axis. The waveform that appears in the electrocardiogram for each heartbeat is mainly composed of five typical waves: a P wave, a Q wave, an R wave, a S wave, and a T wave, in addition to this, U wave exists, and a wave beginning from the Q wave and ending to the S wave may be referred to as a QRS wave. Of these waves, an electrode capable of detecting at least the R wave is preferably provided. The R wave shows the excitement of both the left and right ventricles and is the wave with the largest potential difference. The time from the top of the R wave to the top of the next R wave is generally called R–R time (RRI), and the heart rate per minute can be calculated using the formula (heart rate)=60/(R–R time (seconds)). That is, it is possible to know the heart rate by providing an electrode capable of detecting the R wave and detecting the R wave. In the present invention, the QRS wave is also included in the R wave unless otherwise noted.

The configuration of the present invention will be described below with reference to the drawings. FIGS. 1 and 2 show an example in which the present invention is applied to a T-shirt. FIG. 1 shows the exterior of the T-shirt, and FIG. 2 shows the T-shirt turned back. Electrode support portions 4 are each sewn in accordance with the sewn portion of a front body 2 and a back body 9 of the T-shirt as a bag-binding shape in which both sides are opened by bending a rectangular cloth. Electrodes are in close contact with the side positions of the body, which are relatively preferable positions for electrocardiogram measurement.

FIGS. 3 and 4 are a T-shirt of a type generally called a raglan sleeve type. FIG. 3 shows the exterior, and FIG. 4 shows the raglan sleeve T-shirt turned back. In the example shown here, the electrode support portions are each sewn to the sewn portions of the raglan sleeve portion 9 and the back body 9. In this case, the electrode positions are close to the scapula. Similarly, when the electrode support portions are each sewn to the sewn portion of a raglan sleeve portion 22 and the front body 2, the electrode positions are located substantially on the right and left sides of the pectoral muscle with the heart sandwiched therebetween. The right and left electrode support bodies can be divided into front and rear, and for example, the left side can be sewn to the sewn portion with the back body and the right side can be sewn to the sewn portion with the front body. In addition, by providing electrode support portions at four or more portions of the front, back, right, and left, and in addition, using the sewn portion of the front and back bodies, a plurality of electrodes of three poles or more can be integrated into a single garment without difficulty. In addition, since it does not require a new seam by installing electrodes, the design of a garment and the original comfort are not impaired.

In addition, although the case where the electrode support portion is sewn according to the sewn portion of each part constituting the garment is described here, the present invention is not necessarily limited to the form, and when a new seam is allowed, an electrode support body may be sewn to a free position not only in the sewn portions of the parts of the garment.

FIGS. 5 and 6 show an example of the cross-sectional structure of the sewn portion. FIG. 5 shows a case where the electrode support portion is a single leaf, and FIG. 6 shows a case where the electrode support portion has a bag binding structure. In the case of the bag binding structure, there are two joint sides, and when the electrode support portion is a simple rectangle, the two opposing sides are joint sides. The electrode is located at the portion in direct contact with the body inside the garment. Although omitted in the figure, a wiring and/or a connector 63 is preferably connected to the electrode.

FIG. 7 is a schematic view showing the positional relationship when the joint side of the electrode support portion of the single leaf is sewn at the same portion as the sewn portion of the front body and the back body in the present invention. As an example, the joint side is sewn to the front body and the back body, but as long as it is sewing for constituting the garment, the joint side may be sewn anywhere, and the place to be sewn is preferably selected so that the electrode is arranged at the preferred position for electrocardiogram measurement or myoelectric measurement or in the vicinity thereof. In this example, the electrode support portion is shown in a simplified manner, but a structure in which a plurality of materials are sewn or bonded as a base material may be used.

Here, the shortest distance between the joint side (sewn portion) of the base material of the electrode support portion and the electrode is given by a straight line of double-ended arrows in FIG. 7. In the present invention in which this distance is a part that allows deviation (or play) between the electrode and the garment, this distance is not particularly limited, but is preferably in the range of 3 mm or more and 50 mm or less, preferably in the range of 5 mm or more and 45 mm or less, more preferably in the range of 10 mm or more and 40 mm or less.

FIG. 8 is a schematic view showing a state in which an electrode support portion having a bag binding structure is sewn in an L seam structure (horizontal bonding, side seam, side bonding) as in FIG. 7. Here, the shortest distance between the joint side (sewn portion) of the base material of the electrode support portion and the electrode is given by a straight line of double-ended arrows in FIG. 8 as in the case of FIG. 7. In the case of the bag binding structure, a detachable electronic unit may be arranged without a bag. Wirings, connectors, and the like are designed to suit the purpose.

FIG. 9 is a schematic view showing a case where the electrode support portion having a bag structure is sewn in a center-bonding manner (intermediate bonding, center seam) in the present invention. The electrode position is at a place including the equidistant point from both joint portions, that is, the farthest point from the joint side, before the electrode support portion is bound to the bag. In the figure, a case of a double-open structure (cylindrical structure) is shown, but one side may be sewn into a pocket shape.

FIG. 10 is an example of the case where the electrode support portion having the bag structure of the present invention is used, and it can be preferably adapted to a portion where the deviation in the twisting direction is strong by closing the bag in a conical shape with one opening.

FIG. 11 corresponds to a special example of the case where a single-leaf type electrode support portion is used in the present invention, and is an example in which the electrode support portion is folded into a pocket shape. Although not shown in the figure, it is preferable to sew both sides of the pocket to complete the bag structure. The mouth of the pocket may be on the skin side or on the garment side. The electrode position is appropriately adjusted in each case so as to directly touch the skin of the body. In the case of such a pocket structure, a detachable electronic device may be mounted in the pocket.

On the skin side of the electrode support portion 4 of the present invention, electrode portions 61 for biological information measurement are arranged. When the electrode portion and the wiring portion are made of the same conductive material, the place other than the electrode portion of the conductive material is covered with an insulating sheet material, so that the part not covered with the insulating sheet can be the electrode part and the part covered with the insulating sheet can be the wiring portion.

In the present invention, as another example, an electrode material and a wiring made of a conductive fiber material or the like may be used. As the conductive fiber material, a carbon paste, a conductive rubber sheet, a conductive plastic sheet, or the like can be preferably arranged on the surface of the electrode portion that comes into contact with the skin to optimize the electrical contact impedance with the skin.

The connector 63 is preferably connected to the wiring portion connected to the electrode of the present invention, and the wiring portion is preferably connected to a detachable electronic unit to function as a biological information measuring garment.

It is preferable to use a snap hook as the connector. In addition, when the electronic unit part does not have sufficient water resistance, the detachable electronic unit can be removed and washed at the time of washing the garment, but if the waterproof function on the electronic unit part side is sufficient, it may not be necessarily designed to be removed. In that case, a connecting member that does not require the connector portion to be attached or detached may be used.

In the case of the bag binding structure as a preferred example of the electrode support portion, unpleasant feeling when the end of the free end of the electrode support portion directly touches the skin is reduced. If the material of the electrode support portion is appropriately selected, it is not always necessary to adopt bag binding structure. A reinforcing member 71 may be inserted inside the bag to reinforce the strength of the connector portion. Although the contact point between the snap hook and the wiring portion is crimped, it is preferable that electrical reinforcement is performed so that electrical connection can be reliably obtained with a conductive adhesive, low-temperature solder, or the like. It is also a preferable to sew with a metal wire or conductive fiber.

The above has mainly described the T-shirt as an example of the present invention. The present invention is not limited to the T-shirt, and can be applied in a wide range regardless of whether for men, women, upper body, or lower body.

The garment of the present invention can be applied to garments for armor used in various sports, martial arts, work sites, security, and the like. In addition, the present invention can be applied as hospital garments and care garments in which a caregiver or a medical worker often puts garment on or take garment off a wearer when the wearer is sleeping.

In the present invention, the main material (base material) constituting the garment is a fabric cloth made of a fiber material. Examples of the fabric cloth include woven fabrics, knitted fabrics, and non-woven fabrics. Furthermore, a resin coat, a coated fabric impregnated with a resin, or the like can be used as a base material. A synthetic rubber sheet represented by chloroprene can also be used as a base material. It is preferable that the fabric cloth used in the present invention has stretchability capable of repeatedly expanding and contracting 10% or more. The base material of the present invention preferably has a breaking elongation of 50% or more. The base material of the present invention may be an original fabric, a ribbon or a tape, a braid or a net, or a sheet of cloth cut from the original fabric.

When the fabric cloth is a woven fabric, for example, plain weave, twill weave, satin weave, and the like can be exemplified. When the fabric cloth is a knitted fabric, there can be exemplified, for example, plain knitting and variations thereof, moss stitch, Amundsen knitting, lace knitting, eyelet knitting, splicing net, pile knitting, rib net, ripple knitting, tortoise-shell knitting, blister knitting, Milan rib knitting, double pique knitting, single pique knitting, twill knitting, herringbone knitting, Ponte Roma knitting, basket knitting, tricot knitting, half tricot knitting, satin tricot knitting, double tricot knitting, queen's cord knitting, stripe seersucker knitting, raschel knitting, and tulle mesh knitting, and variations and combinations thereof. The fabric cloth may be a nonwoven fabric made of elastomer fibers.

The fiber material in the present invention is not particularly limited, and natural fibers include cotton, wool, hemp, and the like, and chemical fibers include nylon, acrylic, polyester, polyurethane, and the like. Each of these can be used alone or can be blended at an arbitrary ratio. In the fiber material of the biological information measuring garment of the present application, it is preferable to blend a cotton material in a weight ratio of 25% or more. More preferably, it is preferable to blend a stretchable material in a weight ratio of 5% or more. Preferred blended materials are a blended material of cotton and polyurethane, and a blended material of cotton, polyester, and polyurethane. In particular, the fiber material of the electrode support portion is preferably a material containing cotton in a weight ratio of 35% or more.

The clothing fabric made of the fiber material constituting the garment of the present invention may be either a woven fabric or a knitted fabric (knit), but a camisole with a brassiere illustrated in this example is preferably composed mainly of a knitted fabric.

As a material used for the electric wiring and/or electrode in the present invention, a metal foil, a conductive fabric, a stretchable conductor sheet, and the like can be used. In the electrode portion, an electrode surface layer may be provided as necessary. The wiring portion is preferably covered with an insulating cover layer, preferably a stretchable insulating cover layer. Moreover, a base layer that functions for an adhesive improvement or insulation may be provided at the boundary with the fabric cloth for both the electrode and the wiring.

Next, a case will be described in which the present invention is applied to a garment composed of a plurality of basic parts in which at least the front surface of the garment is divided into upper and lower parts such as a chest part and an abdomen part. Such a form is not particularly limited, but can typically be found in a female camisole with a brassiere (referred to as a bra camisole, or a camisole with a cup, or abbreviated as a bra cami).

An example of the configuration of the present invention will be described below with reference to the drawings. FIGS. 16 to 18 are an example of a camisole with a brassiere that is an example of the garment of the present invention. Hereinafter, an example of a camisole with a brassiere is abbreviated as this example. In this example, the garment is composed of basic parts consisting of a front body 2, a cup portion 3, a back body 9, and a bag cloth 10, and further includes shoulder straps 11 and an engagement portion 7 attached to the bag cloth.

The cup portion in the present invention is a part covering the chest part (or breast in the case of women's garment). A back cup may be attached to the back side (skin side) of the cup portion as needed. The front body in the present invention is a part below the cup on the front side of the body portion. The back body is a part that covers a lower part from the upper part of the waist of the back of the body corresponding to the front body.

In this example, the electrode support portion 4 in the present invention is a part that is located on the skin side on the front side of the body portion and is arranged under the back cup. The upper end of the electrode support portion is overlapped with the sewn portion of the cup portion and the front body and simultaneously sewn (cup portion-side sewn portion 65) to be attached to the garment. On the other hand, the lower side of the electrode support portion is not sewn to the garment body (front body) and is free. In this example, the side portion of the electrode support portion is overlapped with the sewn portion of the front body and the back body or the bag cloth and simultaneously sewn (lateral-side sewn portion 66) so that the electrode support portion is not easily turned back at the time of wearing. It is possible to attach the electrode to the garment without increasing the number of extra seams by sewing the electrode support portion at the same time when the basic parts constituting the garment are sewn.

On the skin side of the electrode support portion 4, the electrodes 61 for biological information measurement are arranged. In this example as a preferable example, the electrode centers are located at approximately 100 mm to 180 mm from the center of the whole body to the right and left, and wiring portions 62 are arranged from the electrodes toward the center of the body. In this example, an example of using a sheet-like electric wiring material is shown, and the wiring portions are rectangular. Although not shown in the figure, the part other than the electrode portion is covered with an insulating sheet material, so that the part not covered with the insulating sheet is the electrode portion and the part covered with the insulating sheet is the wiring portion.

In the present invention, as another example, an electrode material and a wiring made of a conductive fiber material or the like may be used. As the conductive fiber material, a carbon paste, a conductive rubber sheet, a conductive plastic sheet, or the like can be preferably arranged on the surface of the electrode portion that comes into contact with the skin to optimize the electrical contact impedance with the skin.

Stainless steel snap hooks 63 are attached as connectors to a part corresponding to the chest centers of the right and left wiring portions, and are connected to a detachable electronic unit 80 via the connectors.

In this example, as a preferred example, the base portions of the snap hooks are arranged in contact with the wiring portions, and the convex portions of the snap hooks penetrate the electrode support portion and protrude to the opposite side of the electrodes of the electrode support portion. In this manner, the detachable electronic unit can be attached thereto.

When the electronic unit portion does not have sufficient water resistance, the detachable electronic unit can be removed and washed at the time of washing the garment, but if the waterproof function on the electronic unit portion side is sufficient, it may not be necessarily designed to be removed. In that case, a connecting member that does not require the connector portion to be attached or detached may be used.

In this example, as a preferred example, the electrode support portion is folded and bag-sewn to reduce unpleasant feeling when the free end (lower end) of the electrode support portion directly touches the skin. If the material of the electrode support portion is appropriately selected, it is not always necessary to adopt bag sewing. In this example, the reinforcing member 71 may be inserted inside the bag to reinforce the strength of the connector portion. Although the contact point between the snap hook and the wiring portion is crimped, it is preferable that electrical reinforcement is performed so that electrical connection can be reliably obtained with a conductive adhesive, low-temperature solder, or the like. It is also a preferable to sew with a metal wire or conductive fiber.

In this example, as a preferred example, a skin pad 64 is arranged on the skin side of the electrode support portion, particularly on the skin side of the part that overlaps the connector, specifically, the detachable electronic unit to reinforce the connector portion and, at the same time, reduce the unpleasant feeling when the unevenness of the connector or the detachable electronic unit directly touches the skin.

The skin pad may be arranged on the skin side in the vicinity to which the electronic unit of the electrode support portion is attached. The skin pad has an area that can cover at least the connector of the electrode portion. The material of the skin pad is not particularly limited, but a material having flexibility and cushioning characteristic such as a foamed urethane sheet or a foamed rubber sheet is preferable. Foamed chloroprene rubber sheets used for wet suits and the like are materials that can be preferably used. Furthermore, an insulating reinforcing member may be arranged on the connector side of the electrode support portion for reinforcement and insulation protection for the connector part. The materials preferably used as the reinforcing member are a polyurethane sheet, a silicone rubber sheet, and other synthetic rubber sheets and natural rubber sheets.

With such a configuration, the detachable electronic unit can be installed at a position where it cannot be seen from the outside of the garment and does not directly touch the skin. In this example, the hand can easily reach the detachable unit installation portion by putting the hand through the opening along the breast line of the garment, so there is no inconvenience in detaching the detachable unit from the state of wearing the garment.

In this example, a rear opening structure is used as a preferable setting. An engagement portion is attached to the bag cloth of the rear opening portion, and the tightening degree of the garment can be adjusted stepwise or continuously. As a result, the degree of close contact of the electrode support portion with the body can be adjusted as appropriate. The engagement portion is not particularly limited, and for example, a hook, a hook-and-loop fastener, a button, or the like can be used.

The above describes an example of a camisole with a brassiere for women as an example of the present invention. The present invention is not limited to the camisole with a brassiere and can be applied to a wide range regardless of whether the garment is for men or women as long as the garment is composed of a plurality of basic parts in which at least the front surface of the garment is divided into upper and lower parts such as a chest part and an abdomen part.

The metal foil used as the electric wiring in the present invention is preferably one or more metal foils selected from copper foil, phosphor bronze foil, nickel plated copper foil, tin plated copper foil, nickel/gold plated copper foil, aluminum foil, silver foil, and gold foil having a thickness of 50 μm or less, preferably 25 μm or less, more preferably 15 μm or less, more preferably 8 μm or less, still more preferably 4 μm or less, and 0.08 μm or more.

These metal foils can be mud imaged by conventional methods such as electrolysis, electroless, rolling, vapor deposition, and sputtering. Such a metal foil can be processed into a predetermined pattern shape by an etching method, a lift-off method, an additive method, a punching method, a laser cutting method, or the like.

Geometric redundancy in the present invention means that when two points of a point A and a point B are defined in a space, the two points are connected using a path Y longer than the shortest distance X between the two points, so that connection state is maintained with a margin even when the distance between the two points is extended. Where redundancy factor is defined as Redundancy factor=$Y/X$.

The length here is the length of a line passing through the center of a line path having a width.

The redundancy factor in the present invention is preferably 1.41 or more, more preferably 1.8 or more, still more preferably 2.2 or more, and further preferably 2.8 or more. In order to increase the redundancy factor, the metal foil may simply be arranged in a zigzag or sine wave shape or a repeated horseshoe shape.

Such a metal foil preferably having a zigzag pattern can be processed into a predetermined pattern by forming a laminate of a stretchable sheet such as a rubber sheet, a urethane sheet, or a silicone rubber sheet as an example and the metal foil, and then removing unnecessary parts of the metal foil by a subtractive method. The subtractive method is synonymous with an etching method used in a general printed wiring board manufacturing method. The stretchable sheet may serve as the base layer or may function as a part of the base layer.

In the case of using a metal foil as an electrode in the present invention, preferably, the metal foil surface can be protected by noble metal plating with metal such as gold, silver, platinum, rhodium, or ruthenium, or plating with metal that is less susceptible to oxidative deterioration due to passive formation such as chromium, molybdenum, tungsten, nickel, or a corrosion-resistant alloy. An electrode surface protective layer can also be provided by printing carbon paste or the like on the electrode surface. Alternatively, it can be covered with a stretchable conductive composition composed of a conductive filler and a flexible resin.

In the present invention, a conductive thread (including a conductive fiber) can be used as the wiring. It is preferable that the wiring using the conductive thread be combined with an electrode using a conductive fabric. The conductive thread in the present invention refers to a thread having a resistance value of 100Ω or less per 1 cm of fiber length. Here, the conductive thread is a general term for conductive fibers, fiber bundles of conductive fibers, and twisted threads, braided threads, spun threads, and blended threads obtained from fibers containing conductive fibers. As the conductive thread of the present invention, there can be exemplified conductive threads obtained from metal-coated chemical fiber, metal-coated natural fiber, chemical fiber coated with conductive oxide, natural fiber coated with conductive oxide, chemical fiber coated with carbon-based conductive material (graphite, carbon, carbon nanotube, graphene, or the like), natural fiber coated with carbon-based conductive material, chemical fiber coated with conductive polymer, and natural fiber coated with conductive polymer. This type of conductive thread includes a conductive ultrathin slit film obtained by slitting a polymer film coated with one or more conductive materials selected from metal, carbon-based conductive material, conductive metal oxide, and conductive polymer into a width of 800 μm or less.

As the conductive thread in the present invention, there can be used a conductive thread obtained from conductive fiber obtained by spinning a polymer in which one or more conductive materials selected from metal, carbon-based conductive material, conductive metal oxide, and conductive polymer are kneaded.

Further in the present invention. A metal fine wire having a thickness of 250 μm or less, preferably 120 μm or less, more preferably 80 μm or less, and still more preferably 50 μm or less can be used as conductive fiber or a conductive thread. Furthermore, in the present invention, a conductive thread obtained by carrying and impregnating a conductive filler, a conductive polymer, or the like in a fiber bundle such as a microfiber nanofiber can be used.

In the present invention, it is particularly preferable to use one or more conductive threads selected from a metal-coated chemical fiber, a fiber bundle impregnated with a conductive polymer, and a metal fine wire having a thickness of 50 μm or less.

It is preferable that the wiring by the conductive thread has redundancy. Redundancy can be given by a method such as embroidering the conductive thread in a zigzag pattern, for example, or incorporating the conductive thread into a knit, creating a loop in the conductive thread part to ensure redundancy, and using the knit clothing fabric itself as a wiring.

In the present invention, a conductive fabric can be used as the electrode. The conductive fabric in the present invention is a general term for a fibrous structure having conductivity. As an example of the conductive fabric of the present invention, a woven fabric, a knitted fabric, or a non-woven fabric composed of fibers containing conductive threads (including conductive fibers) can be used. Moreover, a conductive fabric can be obtained by embroidering a conductive thread on a non-conductive fabric cloth. Further, a fibrous structure obtained by impregnating a non-conductive fabric cloth with a solution of a conductive polymer or a solution of a composition containing a conductive filler and a binder resin and drying it can be used.

It is preferable to use a fibrous structure impregnated with a conductive polymer as the conductive fabric in the present invention. As the conductive fabric of the present invention, it is preferable to use a conductive fabric in which the fibrous structure is impregnated with the conductive polymer by applying a dispersion liquid in which a conductive polymer and a binder are dispersed in a solvent to the fabric. In the invention, as the conductive polymer, a mixture of poly (3,4-ethylenedioxythiophene) and polystyrene sulfonic acid can be preferably used. In the present invention, it is preferable that the conductive fabric used for the electrode is a woven or knitted fabric, and the basis weight of the woven or knitted fabric is less than 50 g/m$^2$ or more than 300 g/m$^2$. It is preferable that the fabric used for the electrode of the present invention be a synthetic fiber multifilament in which at least a part of the synthetic fiber multifilament is an ultrafine filament having a fineness of less than 30 dtex, or a synthetic fiber multifilament having a fineness exceeding 400 dtex in which a single thread fineness is 0.2 dtex or less.

In the present invention, a stretchable conductor layer (or a stretchable conductor layer sheet) can be used as a material of an electrode and a wiring. The stretchable conductor layer refers to a layer made of a material having stretchability and a specific resistance of $1 \times 10^0$ Ωcm or less. The stretchable conductor layer of the present invention has stretchability. The stretchability in the present invention means that it can repeatedly expand and contract by 10% or more while maintaining conductivity. Further, in the stretchable conductor layer of the present invention, the conductor layer alone has a breaking elongation of 40% or more, preferably a breaking elongation of 50% or more, and more preferably a breaking elongation of 80% or more. Further, the stretchable conductor layer of the present invention preferably has a tensile modulus of 10 to 500 MPa. A material capable of forming such a stretchable conductor layer having stretchability is called a stretchable conductor composition.

The stretchable conductor composition can be obtained through a conductive paste described below. Hereinafter, a conductive paste which is one of means for realizing the constituent elements of the present invention will be described. The conductive paste is composed of at least conductive particles, a stretchable resin, and a solvent.

The conductive particles of the present invention are particles having a particle diameter of 100 μm or less which are made of substances having a specific resistance of $1 \times 10^{-1}$ Ωcm or less. Examples of the material having a specific resistance of $1 \times 10^{-1}$ Ωcm or less include metal, alloy, carbon, doped semiconductor, conductive polymer, and the like. As the conductive particles preferably used in the present invention, there can be used metals such as silver, gold, platinum, palladium, copper, nickel, aluminum, zinc, lead, and tin, alloy particles such as brass, bronze, white copper, and solder, hybrid particles such as silver-coated copper, metal-plated polymer particles, metal-plated glass particles, metal-coated ceramic particles, and the like.

In the present invention, it is preferable to use flaky silver particles or amorphous aggregated silver powder. The particle size of the flaky powder is not particularly limited, but those having an average particle size (50% D) measured by a dynamic light scattering method of 0.5 to 20 μm are preferable. More preferably, it is 3 to 12 μm. When the average particle size exceeds 15 μm, it becomes difficult to form a fine wiring, and clogging occurs in the case of screen printing. When the average particle size is less than 0.5 μm, it is impossible to make contact between particles at low filling, and conductivity may deteriorate. The particle size of the amorphous aggregated powder is not particularly limited, but those having an average particle size (50% D) measured by a light scattering method of 1 to 20 μm are preferable. More preferably, it is 3 to 12 μm. When the average particle size exceeds 20 μm, dispersibility is lowered and pasting becomes difficult. When the average particle size is less than 1 μm, the effect as agglomerated powder is lost, and good conductivity may not be maintained at low filling.

Examples of the flexible resin in the present invention include thermoplastic resin, thermosetting resin, rubber, and the like having an elastic modulus of 1 to 1000 MPa, and rubber is preferable in order to exhibit film stretchability. Examples of the rubber include urethane rubber, acrylic rubber, silicone rubber, butadiene rubber, nitrile group-containing rubber such as nitrile rubber and hydrogenated nitrile rubber, isoprene rubber, vulcanized rubber, styrene butadiene rubber, butyl rubber, chlorosulfonated polyethylene rubber, ethylene propylene rubber, vinylidene fluoride copolymer, and the like. Among these, nitrile group-containing rubber, chloroprene rubber, and chlorosulfonated polyethylene rubber are preferable, and nitrile group-containing rubber is particularly preferable. In the present invention, the elastic modulus is preferably in the range of 3 to 600 MPa, more preferably 10 to 500 MPa, and still more preferably 30 to 300 MPa.

The rubber containing a nitrile group is not particularly limited as long as it is rubber or elastomer containing a nitrile group, but nitrile rubber and hydrogenated nitrile rubber are preferred. Nitrile rubber is a copolymer of butadiene and acrylonitrile. If the amount of bound acrylonitrile is large, the affinity with metal increases, but the rubber elasticity contributing to stretchability decreases conversely. Accordingly, the amount of bound acrylonitrile in the acrylonitrile butadiene copolymer rubber is preferably 18 to 50% by mass, and particularly preferably 40 to 50% by mass.

The blending amount of the flexible resin in the present invention is 7 to 35% by mass, preferably 9 to 28% by mass, and more preferably 12 to 20% by mass with respect to the total of the conductive particles and the flexible resin. The solvent is not limited, and a known organic solvent or aqueous solvent may be used.

The base layer of the present invention is a layer that functions for insulation on the base material side of the wiring portion. Here, the insulation includes mechanical, chemical, and biological insulation in addition to electrical insulation, and requires a function of insulating the conductor layer from moisture, chemical substances, and biological substances that permeate the base material.

The base layer of the present invention is preferably a flexible polymer material. As the flexible polymer material, a so-called rubber or elastomer material can be used. As the rubber and elastomer of the present invention, a resin material exemplified as a flexible resin used in the stretchable conductor composition can be preferably used.

It is preferable that the base layer of the present invention has stretchability capable of repeatedly expanding and contracting 10% or more. The base layer of the present invention preferably has a breaking elongation of 50% or more. Further, the base layer of the present invention preferably has a tensile elastic modulus of 10 to 500 MPa.

The base layer of the present invention is preferably applied to the base material via a coating liquid, an immersion liquid, a printing ink, or a printing paste in a liquid form or a slurry state. It is also possible to form a sheet in a separate process in advance and bond it to the fabric cloth by a method such as hot pressing.

The electrical wiring of the present invention is preferably covered with an insulating cover coat layer. The cover coat layer can be made of a stretchable resin material or the like similarly to the base layer.

The detachable electronic unit in the present invention has a function of receiving and measuring at least an electric signal obtained from an electrode in contact with a biological body via a wiring and a connector, and more preferably is a small electronic unit having a calculation function, a display function, a storage function, and a communication function. In the present invention, it is preferable to use a detachable electronic unit having a function of communicating a biological signal AD-converted by a function based on an existing communication standard or the like to an external device.

EXAMPLES

The present invention is more specifically described by way of the following examples. However, the present invention is not naturally limited to the following examples, and as a matter of course, can be appropriately modified and implemented within the scope of complying with the gist of the descriptions above and below. Those all fall within the technical scope of the present invention.

The insulating layer forming resin and the conductive paste used in the following examples were prepared as follows.

[Adjustment of Conductive Paste]

Using Coatron KYU-1 (glass transition temperature −35° C.) manufactured by Sanyo Chemical Industries, Ltd. as a binder, fine silver powder SPH02J (average particle size 1.2 μm) manufactured by Mitsui Mining & Smelting Co., Ltd. as silver particles, Ketjen Black EC600JD manufactured by Lion Specialty Chemicals Co., Ltd., as carbon particles, and butyl carbitol acetate as a solvent, a conductive paste for forming a stretchable conductor was adjusted in a blend of 10 parts by mass of binder, 70 parts by mass of silver particles, 1 part by mass of carbon particles, and 19 parts by mass of solvent. First, the binder resin was dissolved in a solvent half of a predetermined solvent amount, and the resulting solution was added with metal particles and carbon particles. After premixing, the mixture was dispersed in a three-roll mill to be pasted.

The resulting paste for forming a stretchable conductor was screen-printed to a thickness of 25 μm and dried at 100° C. for 20 minutes to obtain a stretchable conductor layer (stretchable conductor sheet) having an initial specific resistance of 250 μΩ·cm and having stretchability to maintain conductivity even after 20% stretching was repeated 100 times.

[Preparation of Stretchable Carbon Paste]

A carbon paste for an electrode protective layer was prepared according to the composition shown in Table 2.

Dispersed were 40 parts by mass of nitrile butadiene rubber resin with a glass transition temperature of −19° C., 20 parts by mass of Ketjen Black EC300J manufactured by Lion Specialty Chemicals Co., Ltd., and 50 parts by mass of ethylene glycol monoethyl ether acetate as a solvent in a three-roll mill after preliminary nucleic acid to obtain a stretchable carbon paste.

Example 1

On a PET release sheet whose surface had been processed with a silicone mold release agent, stretchable carbon paste was screen-printed as an electrode portion, and stretchable conductor paste was printed further thereon. Then, a double-sided hot-melt sheet (corresponding to an insulating base layer) was laminated to form an electrode on the release sheet.

A knit clothing fabric using a polyester-cotton-polyurethane blend thread was used as a base material for the electrode support portion, and the electrode obtained previously on the base material was transferred from the release sheet to a predetermined position on the base material using an iron. Further, silver coated paper was embroidered in a zigzag pattern from the electrode portion to the sewn portion (connection end) of the base material to form a wiring.

Next, the T-shirt having the structure shown in FIGS. 1 and 2 made of a knit clothing fabric using a polyester-cotton-polyurethane blend thread was used as a garment, and the electrode support portion was sewn at the same time as the bag binding structure shown in FIG. 8 at the sewn portion of the front body and the back body. The shortest distance between the connection end (sewn portion) and the electrode end was 5 mm. Furthermore, the wiring of the silver coat thread was pulled to the back neck portion to pass from the seam of the lateral region of the abdomen between the front body and the back body through the seam of the sleeve and back body using the seam of the shoulder part between the front body and the back body so as to overlap the wiring drawn out by the silver coat thread from the electrode, and was connected with a snap hook (connector) for connection with the detachable electronic unit attached to the back neck portion to obtain a biological information measuring garment of T-shirt type. FIG. 12 shows a photograph of the obtained biological information measuring garment, and FIG. 13 shows an enlarged photograph of the vicinity of the electrode support portion.

Comparative Example 1

As Comparative Example 1, with use of the same material as in Example 1, biological information measuring garment of raglan sleeve type T-shirt type was manufactured by sewing in the same manner except that the periphery of the electrode support portion was all sewn to the garment in the structure shown in FIGS. 1 and 2.

The heart rate sensor WHS-2 manufactured by Union Tool Co., which had a wireless data transmission function to a smartphone, was connected to the T-shirt types obtained in the example and the comparative example as detachable electronic units, an electrocardiogram signal was sent to a smartphone from WHS-2 simultaneously with measurement, heart rate data was received by a smartphone manufactured by Apple Inc. incorporating the app "myBeat" dedicated to the heart rate sensor WHS-2, setting was made so that the data can be displayed on the screen, and RRI (ms (millisecond)) and HR (bpm (heart rate/minute)) could be measured. RRI is the time interval between the R wave, which is the wave with the largest potential difference in the electrocardiogram, and the next R wave, and (Heart rate) =60/(R–R time (seconds)) [bpm] can be calculated from RRI. As described above, an electrocardiogram information measurement system using a biological information measuring garment having a heart rate measurement function was configured.

[Wearing and Exercise Test]

A subject was allowed to wear each biological information measurement garment obtained in Example 1 and Comparative Example 1 and exercised according to the operation protocol shown in Table 1, and RRI and HR were measured during that time. The test conditions are as follows.

Test environment 20° C. 50% (At the end of the operation protocol, the subject is not sweating)

Press the electrode portion by hand at the start of the protocol, and do not hold it by hand until the end.

Measure the garment pressure on the electrode portion and the armpit before starting and make adjustment so that the electrode portion is 0.8±0.05 kPa the armpit is 0.7±0.05 kPa.

After the wearing and exercise test, the subject is given sufficient rest for 20 minutes or more before the next test.

TABLE 1

| Seconds | Operation contents | Details |
|---|---|---|
| 0-30 Seating | Arm: Knee | |
| 31-60 | Arm: Resting chin in hand on desk | |
| 61-90 | Recurving (hand: hip) | Recurving for five seconds → Resting for five seconds |
| 91-120 | Stretching (hand: up → down) | Recurving for five seconds (hand: up) → Resting for five seconds (hand: down) |
| 121-150 | Bending down | Bending down for two seconds and returning to seating for two seconds |
| 151-180 Standing | Arm: Up → Down | Up (one second) → Down (one second) * Frontward direction |
| 181-210 | Arm: Side → Down | Side (one second) → Down (one second) |
| 211-240 | Arm: Front → Side | Front (one second) → Side (one second) |
| 241-270 | Bending down | Bending down for two seconds and returning to standing for two seconds |
| 271-300 Stepping | Arm: Up → Down | Up (one second) → Down (one second) * Frontward direction |
| 301-330 | Arm: Front → Side | Front (one second) → Side (one second) |
| 331-360 Jumping | Arm: Down | Per second |
| 361-390 | Arm: Up → Down | Up (one second) → Down (one second) * Frontward direction |
| 391-420 | Arm: Front → Side | Front (one second) → Side (one second) |
| 421-450 Step ladder | Waving arm (not performed) | |
| 451-480 | Waving arm (performed) | |

The obtained test results are shown in FIGS. 14 and 15. FIG. 14 shows measurement results when the biological information measuring garment of the example is worn. Although the measured values vary slightly at the timing of raising and lowering the arm, it can be seen that generally stable measurement can be performed.

FIG. 15 shows the measurement results when the biological information measuring garment of the comparative example is worn. Variations in measured values occur not only when the arm is moved up and down, but also in general exercise, suggesting a phenomenon in which the electrode and skin deviate during exercise.

Example 2

A urethane sheet (corresponding to the insulating cover layer) having a predetermined shape with the electrode part and the connector portion cut out was temporarily bonded to a PET release sheet whose surface had been processed with a silicone mold release agent, and stretchable carbon paste was screen printed on the electrode part. Further, the stretchable conductor paste was printed in a predetermined pattern from the electrode part to the connector position, and a double-sided hot-melt sheet (equivalent to an insulating base layer) was laminated to cover the urethane sheet, to thereby form an electrode and a wiring on the release sheet.

Next, the electrode and the wiring formed on the release sheet obtained in advance were overlaid at a predetermined position of the electrode support portion of the camisole with a brassiere having the structure shown in FIGS. 16 to 20 made of a knit clothing fabric using a polyester-cotton-polyurethane blend thread (so that the double-sided hot-melt sheet was in contact with the clothing fabric of the electrode support portion), and the electrode and wiring were transferred to the electrode support portion together with the insulating base layer and the insulating cover layer by heating and pressurizing by hot pressing. After that, a reinforcing member was installed at a predetermined position so as to have a cross-sectional structure shown in FIG. 20, a snap hook as a connector was attached, and a skin pad was further attached to obtain a camisole with a brassiere having the configuration of the present invention.

Exterior photographs of the obtained camisole with a brassiere are shown in FIGS. 21, 22, and 23. FIG. 21 is an exterior photograph taken from the front side. FIG. 22 is a photograph taken from the rear side in which the engagement portion is disengaged and the rear opening portion is widened so that the electrode support portion can be seen. FIG. 23 is a photograph taken from the rear side in which the engagement portion is disengaged, the rear opening portion is widened, and the electrode support portion is turned back so that the snap hook functioning as a connector can be seen.

Comparative Example 2

As a comparative example, with use of the same material as in the example, a camisole with a brassiere was manufactured by sewing in the same manner except that the electrode support portion was not attached in the structure shown in FIGS. 16 to 18, and the lower part (corresponding to the part where the electrode and the wiring were located when the electrode support portion of the example was provided) of the obtained camisole with a brassiere without the electrode support portion was heated and pressurized by hot pressing as in the example to transfer the electrode and the wiring together with the insulating base layer and the insulating cover layer. Further the snap hook was attached so that the detachable electronic unit was located outside the garment, to thereby obtain the camisole with a brassiere for the comparative example of the present invention.

The heart rate sensor WHS-2 manufactured by Union Tool Co., which had a wireless data transmission function to a smartphone, was connected to the camisoles with a brassiere obtained in Example 2 and Comparative Example 2 as detachable electronic units, an electrocardiogram signal was sent to a smartphone from WHS-2 simultaneously with measurement, heart rate data was received by a smartphone manufactured by Apple Inc. incorporating the app "myBeat" dedicated to the heart rate sensor WHS-2, setting was made so that the data can be displayed on the screen, and RRI (ms (millisecond)) and HR (bpm (heart rate/minute)) could be measured. RRI is the time interval between the R wave, which is the wave with the largest potential difference in the electrocardiogram, and the next R wave, and (Heart rate)=60/(R−R time (seconds)) [bpm] can be calculated from RRI.

As described above, an electrocardiogram information measurement system using a biological information measuring garment (camisole with a brassiere) having a heart rate measurement function was configured.

The wearing and exercise test was conducted below as in Example 1.

The obtained test results are shown in FIGS. 24 and 25. FIG. 24 shows measurement results when the biological information measuring garment of the example is worn. Although the measured values vary slightly at the timing of raising and lowering the arm, it can be seen that generally stable measurement can be performed.

FIG. 15 shows the measurement results when the biological information measuring garment of the comparative example is worn. Variations in measured values occur not only when the arm is moved up and down, but also when the arm is moved frontward and laterally, suggesting a phenomenon in which the electrode and skin deviate particularly due to the lateral movement of the arm.

INDUSTRIAL APPLICABILITY

As described above, the biological information measuring garment of the present invention can be applied to biological information measuring garments with electrodes in a wide range regardless of whether it is for men, women, upper body, or lower body, and can be applied to garments for armor used in various sports, martial arts, work sites, security, and the like. In addition, the present invention can be applied as hospital garments and care garments in which a caregiver or a medical worker often puts garment on or take garment off a wearer when the wearer is sleeping. Furthermore, the biological information measuring garment of the present invention can provide a biological information measuring garment excellent in the exterior design because the presence of parts related to measurement is difficult to be seen from the outside of the garment. Therefore, the biological information measuring garment can be worn more easily, and it is possible to measure biological information with high accuracy at the same time, so that it is expected to contribute greatly to the industry.

DESCRIPTION OF REFERENCE SIGNS

1: biological information measuring garment
2: front body
3: cup portion
4: electrode support portion
5: back cup
6: collar circumference (neck circumference)
7: engagement portion
8: rear opening
9: back body
10: bag cloth
11: shoulder strap
14: sewn portion (sewn position, connection end)
21: sleeve portion
22: raglan sleeve portion
61: electrode
62: wiring portion
63: connector
64: skin pad
65: cup portion-side sewn portion
66: lateral-side sewn portion
71: reinforcing member
80: detachable electronic unit

The invention claimed is:

1. A biological information measuring garment comprising a garment body and an electrode support portion including an electrode for biological information measurement,
wherein the electrode support portion includes a flexible fabric cloth as a base material,
wherein the electrode support portion is located on a side of the garment body configured to be in contact with a biological body,
wherein the base material of the electrode support portion has a joint side fixed to the garment body and a free side not fixed to the garment body,
wherein, the joint side and the free side define a perimeter of the base material of the electrode support portion, such that a length of the joint side is 60% or less of the perimeter of the base material of the electrode support portion,
wherein the base material and the garment body are sewn at at least one part of the joint side,
wherein the electrode has a first surface and a second surface which is opposite to the first surface,
wherein the first surface of the electrode is not in contact with the base material and is configured to be in contact with the biological body, and
wherein the second surface of the electrode is bonded on the base material.

2. The biological information measuring garment according to claim 1, wherein a shortest distance between the joint side of the base material and the electrode is in a range of 3 mm or more and 50 mm or less.

3. The biological information measuring garment according to claim 1,
wherein the biological information measuring garment is a garment including at least a front body and a back body, and
wherein the joint side is sewn at a same position as a sewn portion of the front body and the back body.

4. The biological information measuring garment according to claim 1,
wherein the biological information measuring garment is a garment including at least a sleeve portion and a body portion, and
wherein the joint side is sewn at a same position as a sewn portion of the sleeve portion and the body portion.

5. The biological information measuring garment according to claim 1, wherein the joint side is sewn at a same position as a sewn portion of a neckline of the garment.

6. The biological information measuring garment according to claim 1, wherein the joint side is sewn at a same position as a sewn portion of a cuff of the garment.

7. The biological information measuring garment according to claim 1, wherein the joint side is sewn at a same position as a sewn portion of a portion around a waist of the garment.

8. The biological information measuring garment according to claim 1, wherein the joint side is sewn at a same position as a sewn portion of a hem of the garment.

9. The biological information measuring garment according to claim 1, wherein the base material of the electrode support portion has an open bag structure.

10. The biological information measuring garment according to claim 9, wherein the open bag structure has two or more open portions.

11. The biological information measuring garment according to claim 9, wherein the open bag structure has one open portion.

12. The biological information measuring garment according to claim 9,
wherein the base material of the electrode support portion has the open bag structure, and
wherein a position of the electrode is a location including a farthest position from a sewn portion on the base material.

13. The biological information measuring garment according to claim 1,
wherein the garment body includes at least a cup portion configured to cover a chest part of the biological body, and a front body, and
wherein the cup portion, the front body, and the electrode support portion are sewn at a same position.

14. The biological information measuring garment according to claim 13,
wherein the cup portion includes a front cup portion and a back cup portion, and
wherein the front cup portion is made of the same fiber material as a fiber material of the front body.

15. The biological information measuring garment according to claim 13,
wherein the electrode support portion has a bag structure, and
wherein a closing mouth of the bag is sewn at the same position as the cup portion, the front body, and the electrode support portion.

16. The biological information measuring garment according to claim 13, wherein a connector for connecting the electrode and a detachable electronic unit is located between the electrode support portion and the front body.

17. The biological information measuring garment according to claim 13, wherein a fiber material constituting the front body and the front cup portion is a knit material containing 50% or more of cotton.

18. The biological information measuring garment according to claim 13, wherein the biological information measuring garment has a rear opening structure, and the rear opening structure includes a plurality of engagement portions for adjusting a size of the cup portion.

19. The biological information measuring garment according to claim 13, wherein the electrode includes a wiring, and the electrode and the wiring are made of the same material.

20. The biological information measuring garment according to claim 13, wherein the electrode for biological information measurement is a conductive fabric.

* * * * *